United States Patent [19]

Ito et al.

[11] Patent Number: 4,797,096
[45] Date of Patent: Jan. 10, 1989

[54] MEASURING TOOL FOR THE SELECTION OF ARTIFICIAL TEETH

[75] Inventors: Toshio Ito; Takashi Miwa; Fujio Yamagishi, all of Kasugai, Japan

[73] Assignee: G-C Toshi Kogyo Corporation, Kasugai, Japan

[21] Appl. No.: 3,145

[22] Filed: Jan. 14, 1987

[30] Foreign Application Priority Data

Jan. 29, 1986 [JP] Japan .............................. 61-10250[U]
Oct. 23, 1986 [JP] Japan .............................. 61-252426

[51] Int. Cl.⁴ .............................................. A61C 19/04
[52] U.S. Cl. ......................................... 433/26; 33/514
[58] Field of Search ................. 433/72, 75, 26, 197; 33/513, 514

[56] References Cited

U.S. PATENT DOCUMENTS

| | | | |
|---|---|---|---|
| 1,293,567 | 2/1919 | Stanton | 433/26 |
| 1,800,714 | 4/1931 | Clapp | 33/513 |
| 2,169,719 | 8/1939 | Bush | 433/26 |
| 2,491,136 | 12/1949 | Salzmann | 433/72 |
| 4,610,629 | 9/1986 | Schrems et al. | 433/72 |

Primary Examiner—Gene Mancene
Assistant Examiner—Adriene J. Lepiane
Attorney, Agent, or Firm—Oblon, Fisher, Spivak, McClelland & Maier

[57] ABSTRACT

A measuring tool for the selection of artificial teeth includes a substrate on which at least the full-scale mesiodistal highest position of contour of artificial teeth is indicated with the product classification mark thereof. The substrate is provided on the predetermined positions with a scale for determining the average condyle head at an interval of 13 mm and a scale for judging an angle that the occlusal surface makes with the interalveolar ridge line.

10 Claims, 6 Drawing Sheets

MEASURING TOOL FOR THE SELECTION OF ARTIFICIAL TEETH

FIELD OF THE INVENTION

The present invention relates to a measuring tool for the selection of artificial teeth which allows easy and accurate selection of artificial teeth accommodative to a region in which natural teeth come off (hereinafter referred to as the natural teeth-devoid region), when a denture accommodative to the natural teeth-devoid region is prepared. The present invention relates to a measuring tool for the selection of artificial teeth which allows easy and accurate selection of artificial teeth accommodative to a region in which natural teeth come off, and makes it possible to prepare dentures providing satisfactory occlusion.

STATEMENT OF THE PRIOR ART

In order to prepare a denture by fitting artificial teeth into the natural teeth-devoid region, it is required to select artificial teeth of a size corresponding to that of the natural teeth lost.

Referring to the artificial teeth, for instance, molar teeth having a medium long axis of crown (designated as product classification mark M), the product classification marks, the length of the first premolar teeth and the width of 4 posteriors one side set up are designed as specified in the following table. Thus, the respective teeth are proportionally determined and classified as regards their length and width, and are hence incrementally determined as regards their size.

TABLE

| Product Classfication Marks | Length of the First Premolar Teeth (mm) | Width of 4 Posteriors One Side Set Up (mm) |
|---|---|---|
| 28 M Upper | 8.0 | 28.0 |
| 30 M Upper | 9.0 | 30.0 |
| 32 M Upper | 9.7 | 32.0 |
| 28 M Lower | 7.0 | 30.0 |
| 30 M Lower | 8.5 | 32.0 |
| 32 M Lower | 9.0 | 34.0 |

Anterior teeth are classified by the characteristic features of form. By way of example, the anterior teeth of a square form are broken down into three sizes S3, S4 and S5 wherein S denotes a "square". Thus, the forms of artificial teeth are broken down into 3 to 5 sizes and are ready for use. It is then required to select the artificial teeth in the most accommodative forms and sizes with respect to a space defined by the natural teeth-devoid region.

Heretofore, the most accommodative artificial teeth for the natural teeth-devoid region are selected by:

(1) visually observing the size of a space defined by the natural teeth-devoid region, (2) repeatedly trying to fit actual artificial teeth into a space defined by the natural teeth-devoid region, and (3) measuring the size of a space defined by the natural teeth-devoid region (to obtain measurements, according to which artificial teeth are selected).

However, the aforesaid selection methods have posed problems in connection with operational accuracy, efficiency and sanitation. In addition, there have been economical problems that all the available artificial teeth should be kept at hand, and much room should be required for that purpose.

Especially where two or more continuous natural teeth come off, the selection of the most accommodative artificial teeth for the resulting space is only achieved with sharply increased inaccuracy.

SUMMARY OF THE INVENTION

As a result of extensive and intensive studies made to overcome such problems that the prior art offers, it has been found that if provision is made of a measuring tool for the selection of artificial teeth including a base member or substrate on which the mesiodistal highest position of contour of artificial teeth of at least full size is indicated along with the classification marks of artificial teeth products, it is then possible to easily and accurately select the most accommodative artificial teeth for a space defined by the natural teeth-devoid region by engaging that tool directly with the natural teeth-devoid region for visual observation. Based on such findings, the first aspect of the invention has been accomplished.

Further, the second aspect of the invention has been accomplished by finding that if the scale for determining the average condyle head and the scale for judging an angle that the occlusal surface makes with the interalveolar ridge line are provided on the predetermined positions of the substrate of the measuring tool according to the first aspect of the invention.

More specifically, according to the first aspect of the present invention there is provided a measuring tool for the selection of artificial teeth characterized by including a base member or substrate on which at least the full-scale mesiodistal highest position of contour of artificial teeth is indicated along with the product classification marks of the artificial teeth.

According to the second aspect of the present invention, there is provided a measuring tool for the selection of artificial teeth characterized by including a base member or substrate on which at least the full-scale mesiodistal highest position of contour of artificial teeth is indicated along with the product classification marks of the artificial teeth, and which is provided at the predetermined positions with a 13 mm-interval scale for determining the average condyle head and a scale for judging an angle that the occlusal surface makes with the interalveolar ridge line.

BRIEF DESCRIPTION OF THE DRAWINGS

The present invention will now be explained in further detail with reference to the accompanying drawings which are given by way of example.

DETAILED DESCRIPTION OF THE PREFERRED EMBODIMENTS

Figure 3:
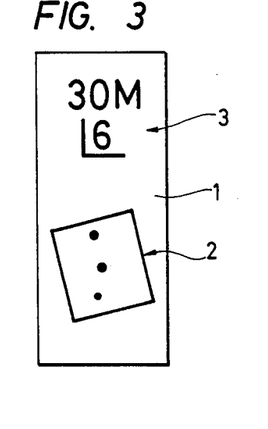
Figure 4:
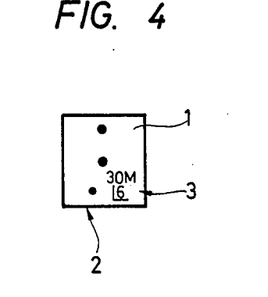
Figure 5:
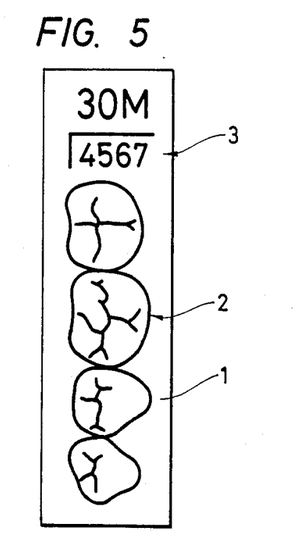
Figure 8:
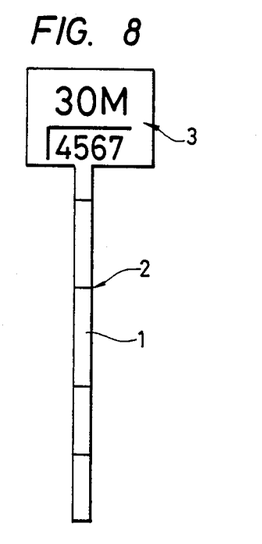
Figure 9:
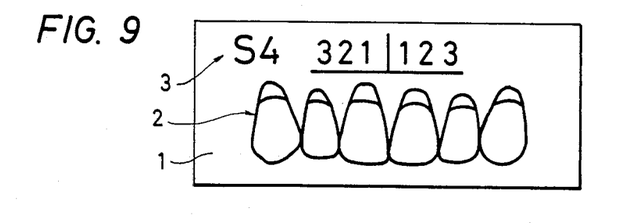
Figure 10:
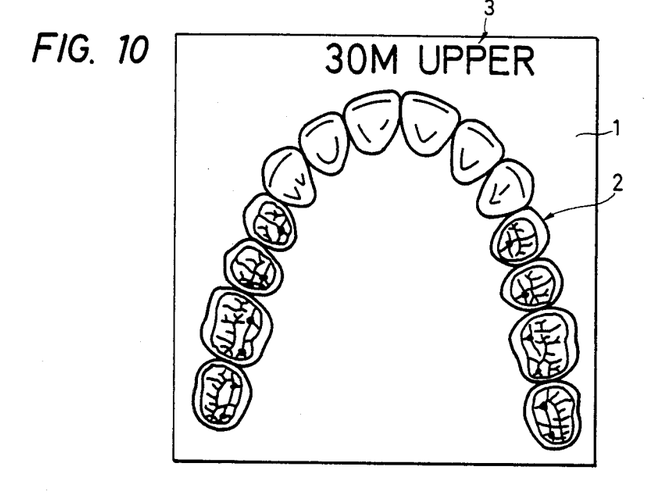
Figure 11:
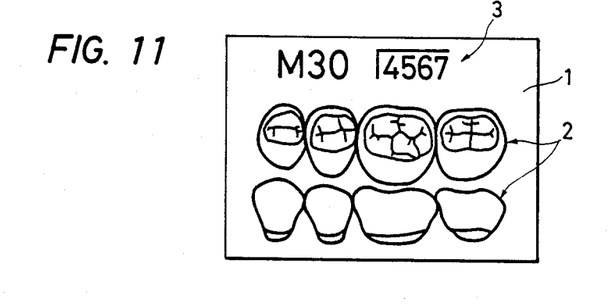
Figure 12:
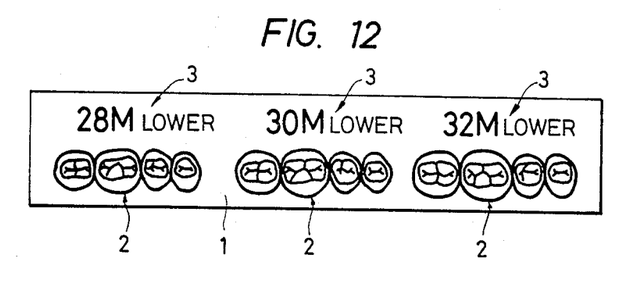
Figure 13:
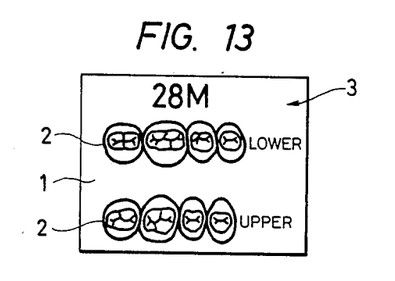
Figure 14:
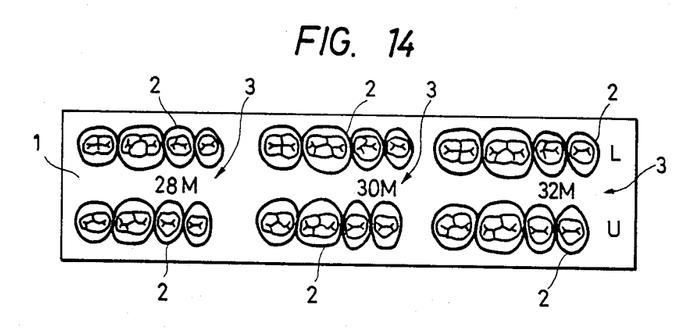
Figure 16:
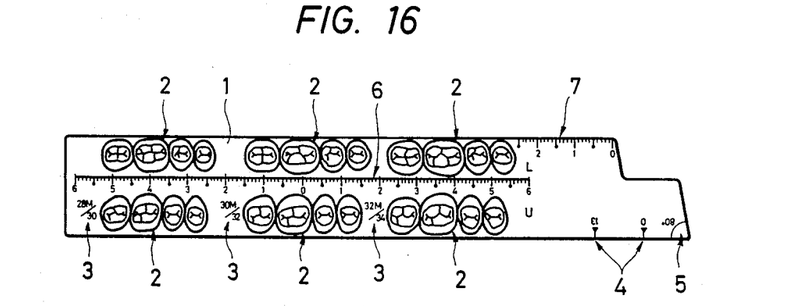
FIGS. 16 to 18 inclusive show the measuring tool for the selection of artificial teeth according to the second aspect of the present invention, FIG. 16 being a plan view showing one embodiment wherein the artificial teeth indicated are in the form of the plan shadow shapes of a set of molar teeth of the upper and lower jaws, which bear different classification marks, FIG. 17 being a view illustrative of the measuring tool for the selection of artificial teeth of FIG. 16, which is used to determine the average condyle head of a patient, and FIG. 18 being a view illustrative of the measuring tool for the selection of artificial teeth of FIG. 16, which is used to judge an angle that the occlusal surface makes with the interalveolar ridge line with a gypsum model.

Referring to the drawings, reference numeral 1 designates a base member or substrate formed of an able-to-see-through materials such as plastics, cellophane paper or glass plates, or an unable-to-see-through materials such as paper, wood, bamboo or metal. It is preferred that the substrate is more or less flexible so that, in actual measurement, it comes into contact with the existing teeth or gingiva and allows easy and accurate selection of the artificial teeth accommodative to the natural teeth-devoid region. The substrate 1 may be colored for easy discrimination of the classification marks of artificial teeth, the upper and lower jaws and the anterior teeth and molar teeth. Reference numeral 2 designates a zone which is provided on the substrate 1, and on which at least the full-scale mesiodistal highest position of contour of artificial teeth is indicated. The number of the artificial teeth indicated on the zone 2 may be one, as shown in FIGS. 1 to 4, or may be plural, as shown in FIGS. 5 to 14. Where the number of the artificial teeth indicated on the zone 2 is two or more, the plurality of the artificial teeth may be a set of the artificial teeth for the upper or lower jaw, which bear the same classification mark, as shown in FIGS. 5 to 11. Alternatively, they may be a set of the artificial teeth for the upper or lower jaw, which bear different classification marks, as illustrated in FIG. 12; a set of the artificial teeth for the upper and lower jaws, which bear the same classification mark, as illustrated in FIG. 13; or a set of the artificial teeth for the upper and lower jaws, which bear different classification marks, as illustrated in FIGS. 14 and 16. Since it is essential in the present invention that at least the mesiodistal highest position of contour of artificial teeth is indicated, they may be indicated in the form of the plan and/or side shadow shapes per se thereof, as illustrated in FIGS. 1, 2, 5–7, 9–14 and 16. Alternatively, they may be indicated in the form of a rectangular shape such as a square or a rectangle defined by parallel lines passing through their highest positions of contour, as illustrated in FIGS. 3 and 4. Still alternatively, only the mesiodistal highest position of contour of artificial teeth may be indicated by parallel lines, as illustrated in FIG. 8. Where the artificial teeth are indicated in the form of a rectangular shape such as a square or a rectangle defined by parallel lines passing through their highest positions of contour, it is preferred that the fissures or cusps are simultaneously indicated by points, as illustrated.

According to the various manners for indicating the artificial teeth on the zone 2, except for the manner depicted in FIG. 8, all the distal, mesial, buccal and lingual highest positions of contour are simultaneously indicated int he form of the plan shadow shape, whereas all the distal, mesial, incisal edge and cervical line highest positions of contour are simultaneously indicated in the form of the side shadow shape. Where the substrate 1 is formed of the unable-to-see-through material, however, it is preferred for the purpose of compensating for the disadvantage of the unable-to-see-through that only the mesiodistal highest position of contour is indicated on the zone 2 by parallel lines, as shown in FIG. 8, or the outer shape of the substrate 1 is formed into the shadow shape of the full-scale artificial teeth to define the zone 2, as illustrated in FIGS. 2 and 6.

Reference numeral 3 designates a classification mark bearing zone on which the classification marks of the artificial teeth products set down on the zone 2 of the substrate 1 are indicated. By way of example, 30M⌊6 set down on the zone 3 in FIGS. 1 to 4 designates the first molar tooth on the left side of the upper jaw, having a medium long axis of crown and a width of 4 posteriors one side set up of 30 mm. 30M⌈4567 set down on the zone 3 in FIGS. 5, 7 and 8 again designates the first premolar tooth, the second premolar tooth, the first molar tooth and the second molar tooth on the left side of the lower jaw, respectively. Further, S4 321|123 set down on the zone 3 in FIG. 9 designates each three anterior teeth in the square form. Still further, 28M, 30M and 32M set down the zone 3 in FIG. 16 designates the molar teeth having a medium long axis of crown and a width of 4 posteriors one side set up of 28 mm, 30 mm and 32 mm, respectively, with "L" and "U" indicating the lower and upper jaws, respectively.

Figure 1:
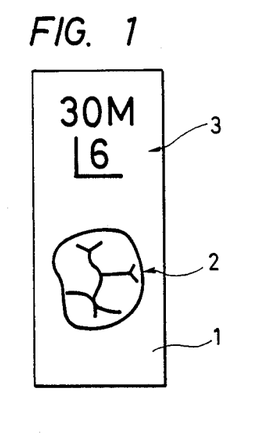
FIGS. 1 to 15 inclusive illustrates the measuring tool for the selection of artificial teeth, FIG. 1 being a plan view showing one embodiment wherein the artificial tooth indicated is in the form of the plan shadow shape of one full-scale molar tooth, FIG. 2 being a plan view showing another embodiment wherein the artificial tooth indicated is in the form of the plan shadow shape of one full-scale molar tooth, FIG. 3 being a plan view showing one embodiment wherein the plane highest position of contour of the molar tooth illustrated in FIG. 1 is indicated in the form of a square defined by parallel lines passing through the full-scale mesiodistal and buccolingual highest positions, FIG. 4 being a plan view showing another embodiment wherein the plane highest position of the contour of the molar tooth illustrated in FIG. 1 is indicated in the form of a square form defined by parallel lines passing through the full-scale mesiodistal and buccolingual highest positions, FIG. 5 being a plan view showing one embodiment wherein the artificial teeth indicated are in the form of the plan shadow shapes of a set of molar teeth for the upper or lower jaw, which bear the same classification mark, FIG. 6 being a plan view showing another embodiment wherein the artificial teeth indicated are in the form of the plan shadow shapes of a set of molar teeth for the upper or lower jaw, which bear the same classification mark, FIG. 7 being a plan view showing another embodiment wherein the artificial teeth indicated are in the form of the side shadow shapes of a set of molar teeth for the upper or lower jaw, which bear the same classification mark, FIG. 8 being a plan view showing one embodiment of a tool wherein only the mesiodistal highest position of contour of artificial teeth is indicated in the form of parallel lines, FIG. 9 being a plan view showing one embodiment wherein the artificial teeth indicated are in the form of the side shadow shape of all the anterior teeth of the upper or lower jaw, which bear the same classification mark, FIG. 10 being a plan view showing one embodiment wherein the artificial teeth indicated are in the form of the plan shadow shape of all the teeth of the upper or lower jaw, which bear the same classification mark, FIG. 11 being a plan view showing one embodiment wherein the artificial teeth indicated are in the form of the plan and side shadow shapes of a set of molar teeth of the upper or lower jaw, which bear the same classification mark, FIG. 12 being a plan view showing one embodiment wherein the artificial teeth indicated are in the form of the plan shadow shapes of a set of molar teeth of the upper or lower jaw, which bear different classification marks, FIG. 13 being a plan view showing one embodiment wherein the artificial teeth indicated are in the form of the plan shadow shapes of a set of molar teeth of the upper and lower jaws, which bear the same classification mark, FIG. 14 being a plan view showing one embodiment wherein the artificial teeth indicated are in the form of the plan shadow shapes of a set of molar teeth of the upper and lower jaws, which bear different classification marks, and FIG. 15 being a view illustrative of the measuring tool for the selection of artificial teeth of FIG. 5 according to the present invention, which is engaged with the natural teeth-devoid region.
Figure 2:
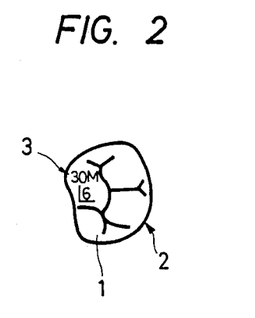
Figure 6:
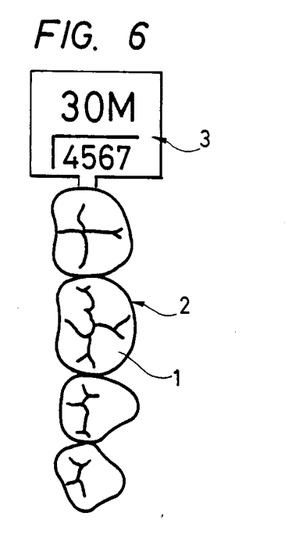
Figure 7:
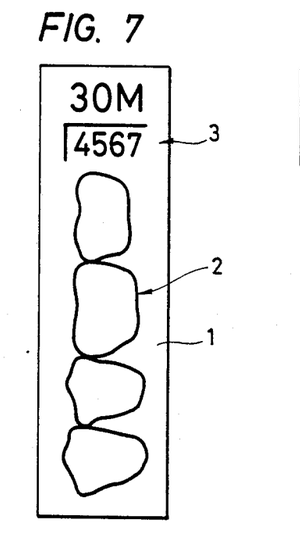

Most generally, to indicate the highest positions of contour and the classification marks on the zones 2 and 3 is achieved by printing, except for the case where the outer shape of the substrate 1 is formed into the outer shape of the full-scale artificial teeth to define the zone 2, as illustrated in FIGS. 2 and 6. However, it is noted that use may be made of various means such as development of photographic films and coloring of artificial teeth portions and the circumferential portions thereof.

Reference numeral 4 stands for a scale for determining the average condyle head provided at an interval of 13 mm on the predetermined position of the substrate 1 of the measuring tool for the selection of artificial teeth according to the second aspect of the present invention.

Reference numeral 5 stands for a scale for judging an angle that the occlusal surface makes with the interalveolar ridge line, which is provided on the predetermined position of the substrate 1 of the measuring tool for the selection of artificial teeth according to the second aspect of the present invention. Preferably, the scale allows judgement of an angle of at least 80° that is the standard angle, on the basis of which whether or not it is required to prepare a denture according to the method of cross bite arrangement is judged. In the embodiment illustrated, the scale is provided at one corner of the substrate 1 in such a manner that it makes an angle of just 80°. However, the scale may be constructed from a protractor including an angle of 80°

Reference numerals 6 and 7 are length scales to be provided on the predetermined positions of the substrate 1, if required. (In the embodiment illustrated, one length scale 6 is located at the center of the substrate 1, while the other length scale 7 is positioned on one side edge of the substrate 1.) Provision of such length scales 6 and 7 is convenient to describe the width of the lip of a patient on a gypsum model and measure the distances of the anterior teeth from the center to the rearmost. Where it is intended to provide such two length scales 6 and 7, it is preferred that the reference position is located at the center of one length scale 6.

Figure 15:
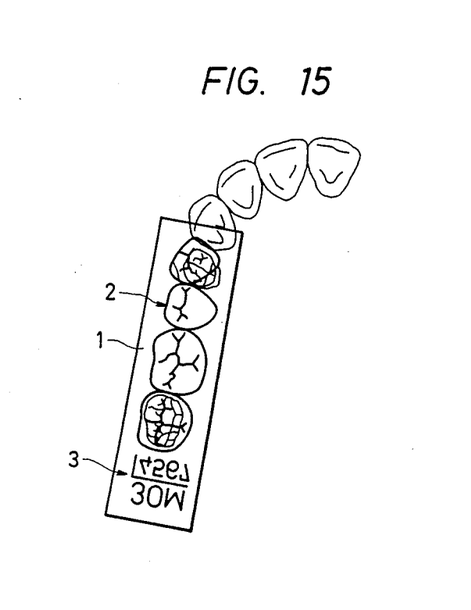

To select the accommodative artificial teeth for the natural teeth-devoid region with the use of the measuring tool for the selection of artificial teeth according to the present invention, it may be inserted into the oral cavity of a patient, or may be engaged with a gypsum model prepared by an impression taken out of the oral cavity of a patient to superimpose the zone 2 upon a space defined by the natural teeth-devoid region, as shown in FIG. 15. Then, whether or not the artificial teeth desired by the zone 2 is in just coincidence with that space is ascertained so as to select the thus ascertained artificial teeth as the most accommodative teeth depending upon the classification mark bearing zone 3. Of the most important requirement in this operation is whether or not the prepared denture has a width to be just fitted into the natural teeth-devoid region. It is thus inevitably essential that at least the full-scale mesiodistal highest position of contour of artificial teeth is indicated on the zone 2. It is then more convenient, if the highest position indicated on the zone 2 is in the form of the plan or side shadow shape, and the buccal and lingual highest positions as well as the incisal edge and cervical line highest positions are simultaneously indicated thereon in addition to the distal and mesial highest positions.

As shown in FIG. 16, in order to select the artificial teeth accommodative to the natural teeth-devoid region with the use of the scale 4 for determining the average condyle head provided on the measuring tool for the selection of artificial teeth according to the present invention, one end of the scale 4 according to the present invention is positioned on the tragus of a patient to find out a position indicating an interval of 13 mm of the scale 4 on a line obtained by connecting the tragus with the caput, which positions are in turn marked. Then, the condylar rod of a GYSI Simplex type or HANAU type articulator to accurately measure a distance between a bite plate supported on a bite fork and the condyle head of the patient. In this manner, it is possible to determine the occlusal state between the artificial teeth of the dentures for the upper and lower jaws and select the artificial teeth in which the incisal and lingual highest positions are optimized for the preparation of dentures providing satisfactory occlusion.

Figure 17:
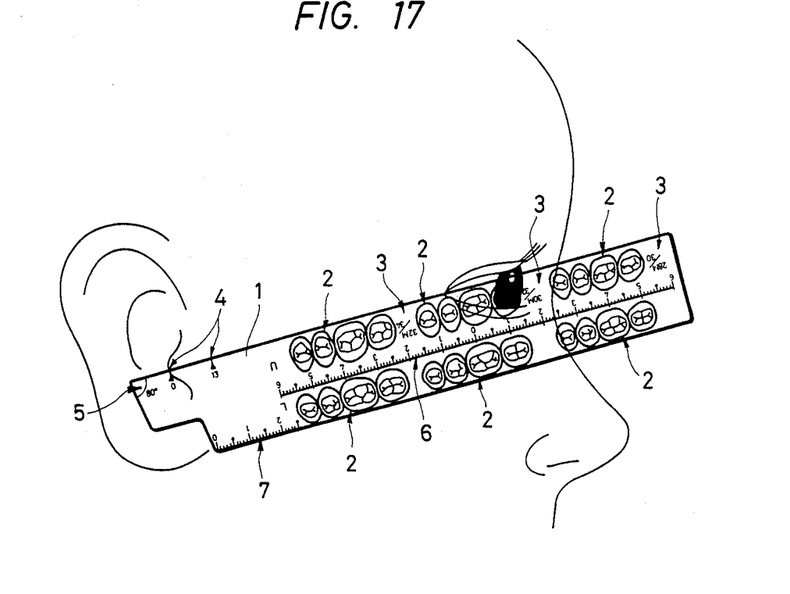
Figure 18:
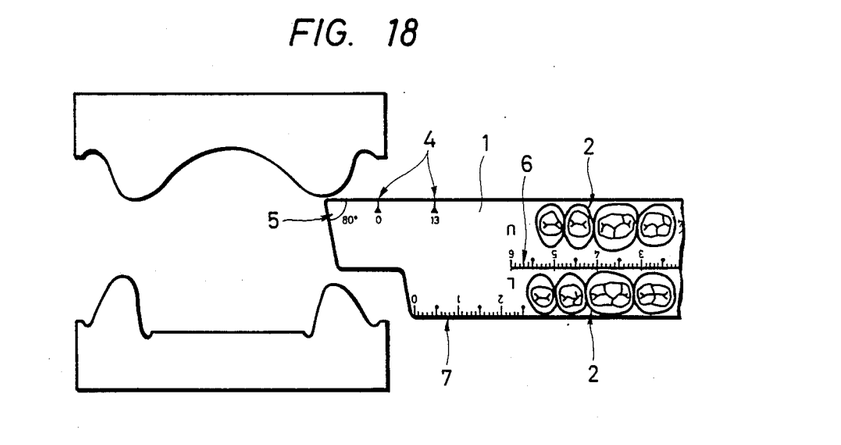

As shown in FIG. 17, to select the artificial teeth accommodative to the natural teeth-devoid region with the use of the scale 5 for judging an angle that the occlusal surface makes with the interalveolar ridge line, which is provided on the measuring tool for the selection of artificial teeth according to the present invention, an angle that the occlusal surface makes with the interalveolar ridge line between the upper and lower alveoluses mounted on a gypsum model is measured with that scale 5. In this manner, it is possible to select the artificial teeth of an angle of inclination providing satisfactory occlusion or make judgement as to whether or not the method of cross bit arrangement is needed.

The measuring tools for the selection of artificial teeth according to the present invention, as described in detail in the foregoing, have the following many advantages and are thus of extremely high practicality.

(1) If the substrate is formed of a thin-plate or rod-like materials, then it is possible to accommodate all the variety of available artificial teeth in a considerably limited space and hence at a lower cost.

(2) The inventive tools can easily be manipulated with high accuracy, since the most accommodative artificial teeth for a space defined by the natural teeth-devoid region can visually be observed in the mouth cavity of a patient or on a gypsum model in a state where they are just actually set in place.

(3) The inventive tools are safe in view of sanitation. This is because after they have been inserted into the mouth cavity of a patient for measurement, they may be disposed on account of their low cost.

(4) The inventive tools allow considerably high selection of artificial teeth, especially where two or more continuous natural teeth come off.

(5) The inventive tools are economical. This is because if the substrate is formed of an able-to-see-through material, it is then possible to measure the artificial teeth for the right side and the left side of a jaw with a single plate by turning it inside out.

(6) Medical costs are low, since it is unnecessary to always hold a variety of available artificial teeth in dental clinics, etc.

(7) With the inventive tools provided with the scale for determining the average condyle head at an interval of 13 mm and the scale for judging an angle that the occlusal surface makes with the interalveolar ridge line, both formed on the predetermined positions of the substrate, it is possible to prepare a denture with more satisfactory occlusion, since the occlusion can be ascertained with a gypsum model.

What is claimed is:

1. A measuring tool for the selection of artificial teeth having a full-scale mesiodistal highest position of contour, said measuring tool comprising:
   (a) a flexible substrate sized and shaped to be inserted into a patient's mouth or into an impression of a patient's mouth and to contact the existing teeth or gingiva to allow easy and accurate selection of artificial teeth for that patient:
   (b) at least the full-scale mesiodistal highest position of contour of a plurality of artificial teeth indicated on said substrate;
   (c) a product classification mark corresponding to the full-scale mesiodistal highest position of contour of said plurality of artificial teeth indicated on said substrate;
   (d) a scale located at an interval of 13 mm for determining the average condyle indicated on said substrate; and
   (e) a scale for judging the angle that the occlusal surface makes with the interalveolar ridge line indicated on said substrate.

2. The tool as recited in claim 1, wherein the plurality of the artificial teeth is a set of artificial teeth for the upper or lower jaw, which bear the same classification mark.

3. The tool as recited in claim 1, wherein the plurality of the artificial teeth is a set of artificial teeth for the upper and lower jaws, which bear the same classification mark.

4. The tool as recited in claim 1, wherein the plurality of the artificial teeth is a set of artificial teeth for the upper or lower jaw, which bear different classification marks.

5. The tool as recited in claim 1, wherein the plurality of the artificial teeth is a set of artificial teeth for the upper and lower jaws, which bear different classification marks.

6. The tool as recited in any one of claims 1 and 2-5, wherein at least the full-scale mesiodistal highest position of contour indicated on said substrate is indicated in the form of the plan shadow shape of artificial teeth.

7. The tool as recited in any one of claims 1 and 2-5, wherein at least the full-scale mesiodistal highest position of contour indicated on said substrate is indicated in the form of the side shadow shape of artificial teeth.

8. The tool as recited in any one of claims 1 and 2-5, wherein at least the full-scale mesiodistal highest position of contour indicated on said substrate is indicated in the form of the plan and side shadow shapes of artificial teeth.

9. The tool as recited in any one of claims 1 and 2-5, wherein said substrate is formed of an able-to-see-through material.

10. The tool as recited in any one of claims 1 and 2-5, wherein said scale for judging an angle that the occlusal surface makes with the interalveolar ridge line permits judgement of at least 80°.

* * * * *